United States Patent [19]

Pless et al.

[11] Patent Number: 4,599,523
[45] Date of Patent: Jul. 8, 1986

[54] POWER PRIORITY SYSTEM

[75] Inventors: Benjamin D. Pless; Lawrence J. Stotts, both of Lake Jackson, Tex.

[73] Assignee: Intermedics, Inc., Freeport, Tex.

[21] Appl. No.: 580,898

[22] Filed: Feb. 16, 1984

[51] Int. Cl.[4] .................. H02J 1/14; A61N 1/378
[52] U.S. Cl. .................................. 307/31; 307/38; 307/41; 128/419 PS
[58] Field of Search .............. 307/20, 23, 31, 34, 307/38, 41; 128/419 PS, 419 PG

[56] References Cited

U.S. PATENT DOCUMENTS 4,345,604  8/1982  Renirie ................. 128/419 PS
4,408,607 10/1983  Maurer ................. 128/419
4,462,407  7/1984  Herscovici et al. ...... 129/419 PS X Primary Examiner—A. D. Pellinen
Assistant Examiner—Derek S. Jennings
Attorney, Agent, or Firm—Willian Brinks Olds Hofer Gilson & Lione Ltd.

[57] ABSTRACT

A priority switching circuit for providing a minimum voltage to a voltage sensitive load while charging a second load drawing a high current includes a battery, comparator, capacitor, and a voltage regulator. The output of the comparator causes the battery to be connected to the capacitor whenever the voltage across the capacitor drops below a predetermined minimum and causes the battery to be connected to the high current load when the voltage across the capacitor rises to a predetermined maximum. The circuit provides a varied switching frequency as the internal impedance of the battery increases with age. The voltage regulator provides a constant reference voltage which is used by the comparator to provide the switching control signals.

20 Claims, 13 Drawing Figures $V_{oc}$ = Open Current Battery Voltage
$V_{min}$ = Minimum Operating Voltage
$A_p$ = Atrial Pace Event
$V_p$ = Ventricular Pace Event

POWER PRIORITY SYSTEM

TECHNICAL FIELD

The invention relates to a power control system for use in any device which contains a single power supply to power two loads, a first load for performing a predefined function, and a control load for controlling the operation of the first load wherein the voltage powering the control load must be maintained above a minimum operating voltage. More particularly the invention relates to the use of such power control systems in body function assistance devices such a heart pacemakers.

BACKGROUND OF THE INVENTION

Modern pacemakers are typically made up of three primary components: a control circuit, an output circuit, and a power source. The control circuit determines the rate, synchronization, pulse width, and output voltage of heart stimulating pulses that are generated by the pacemaker. The control circuit may also perform diagnostic functions which are necessary to the safe operation of the pacer. For example, the circuit may provide backup functions in the event of a failure that could result in dangerous overstimulation or a potentially fatal non-stimulation of the heart. The control circuit is therefore an essential operating component which must be fully operational throughout the life of the pacer.

The power source, typically a lithium iodide battery, is chosen for its high energy density and its low self discharge characteristics. The lithium iodide battery has an internal impedance that increases as current is drawn from it. Therefore, if a constant current is drawn from the battery, the output voltage declines with time even though the unloaded voltage of the battery is very nearly unchanged. The internal impedance makes it impossible to deliver the amount of current required to stimulate the heart directly from the battery. Consequently, the output circuit uses an output capacitor which is charged between pace events and, upon command from the control circuit, discharged for a fixed length of time (usually 0.3 to 1.5 milliseconds) into the heart to stimulate it.

In prior art pacemakers, the battery is connected at all times to both the control circuit and the output circuit. The control circuit, which typically comprises digital circuitry and today may be microprocessor based, draws relatively little power from the battery, but must be continuously supplied. The output circuit, on the other hand, requires a relatively large amount of power but draws it most heavily during a peak demand period after the heart has been paced. The large power drain after pacing is required to recharge the output capacitor as quickly as possible.

As the output capacitor is recharged, there is a drop in battery voltage due to the charging current flowing through the battery impedance. This voltage drop is negligible when the battery is fresh. However, as the battery ages its impedance increases and the voltage drop increases proportionately. Thus, the battery voltage to the control circuit may drop below a minimum operating level when the output capacitor is being recharged. This temporary drop in voltage can cause a potentially dangerous intermittent malfunction of the control circuit and corresponding erratic operation of the pacer. Prior art pacemakers must be removed and replaced before such low voltage malfunctions occur, even though the battery may still be capable of supplying energy sufficient to stimulate the heart.

It can be seen, therefore, that the reliability of prior art pacemakers is compromised at the end of their lifetime. The decreased reliability is not based on the failure of the pacemaker to perform its primary function, i.e. to stimulate the heart, but because of fluctuations in battery voltage below the minimum allowable operating voltage of the control circuit. Thus, pacemaker reliability can be increased by reducing the likelihood that the voltage powering the control circuit will fall below its minimum allowable operating voltage.

Furthermore, the longevity of prior art pacemakers is reduced because transient low voltage conditions require removal of such pacemakers even though the average output voltage of the battery may be sufficient to supply the average demand of the control circuit and the output circuit. Thus, prior art pacers are inefficient in operation. Since longevity is also an important consideration in implantable pacers, it is desirable to increase the useful life of a pacer and its battery as much as possible by efficiently utilizing battery power.

SUMMARY OF THE INVENTION

It is therefore an object of the invention to provide a heart pacemaker with a power distribution controller which reliably provides operating voltage for the control circuit of a pacemaker.

It is another object of the invention to increase the operational reliability and longevity of a body function assistance device through the use of an efficient power control system.

It is a further object of the invention to provide a pacemaker which operates with lower current consumption than prior art pacers.

These and other objects of the invention are achieved through the use of a novel power distribution controller. The power distribution controller regulates the load placed on the power source by selectively switching the power source between a pacemaker output circuit and a pacemaker control circuit.

A hold-up capacitor is connected in parallel with the control circuit in order to maintain at least a minimum operating voltage when the power source is disconnected from the control circuit and connected to power the output circuit. Thus, the hold-up capacitor provides power to the control circuit while the output capacitor of the output circuit is drawing maximum recharging current from the battery.

To further enhance the reliability of the pacemaker, priority may be given to keeping a minimum operating voltage on the hold-up capacitor and across the control circuit. This assures that the control circuit will continue to operate for the longest possible time, and to the maximum possible battery impedance, independent of output parameters such as lead resistance, rate or pulsewidth. Thus, the end of service behavior of the pacemaker is predictable and therefore is more reliable than in prior art pacemakers.

An advantage of the disclosed invention is that the control circuit is isolated from the battery when the output circuit is drawing current. Therefore, the output circuit can draw a maximum amount of current, limited only by the impedance of the battery, without disturbing the operation of the control circuit. This allows the output capacitor to charge more quickly than is otherwise possible.

Another advantage is increased longevity of the pacemaker. Since temporary battery drains cannot affect the control circuit, the end of service determination can be made solely on the basis of whether or not the output circuit is still able to stimulate the heart, thus prolonging the service life of the pacemaker.

A further advantage of the invention, which also contributes to increased longevity of the pacemaker, is a decrease in current consumption by the control circuitry. The invention has an inherent voltage regulating capability which operates the control circuitry at its minimum operating voltage, thus minimizing power consumption.

The invention, together with further objects and advantages, will be best understood with reference to the following description taken in conjunction with the accompanying drawings:

DETAILED DESCRIPTION

Figure 1:
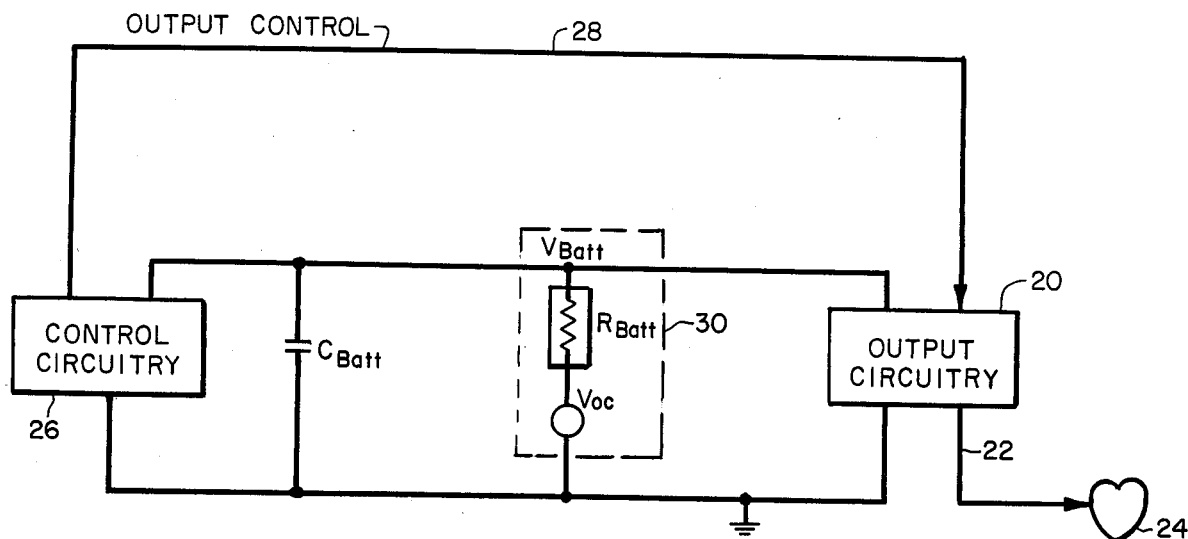
FIG. 1 is a diagrammatic illustration of a prior art pacemaker circuit.

Referring now to the drawings, FIG. 1 illustrates a typical prior art pacemaker circuit. The output circuitry 20 provides electrical impulses along an electrode 22 which is conductively connected to the heart 24. These electrical pulses pace the heart to keep it beating regularly. The control circuitry 26 controls the operation of the output circuitry 20 by transmitting output control signals on control lines 28. The control circuitry 26 determines the pacing rate, synchronization, pulse width, and output voltage for pacing signals generated by the output circuit 20. The control circuit 26 also comprises the cardiac sensing circuit for sensing the atria or the ventricles or both. Synchronization of the pacing is made in reference to the sensed cardiac signals. Furthermore, control circuit 26 may also have diagnostic capabilities for such functions as detecting and preventing pacemaker runaway.

In order for the output circuitry 20 to deliver relatively high current pacing pulses, an output capacitor (not shown) is included in the output circuitry 20. In operation, the output capacitor charges until a signal is received from the control circuitry 26 to pace the heart. When this signal is received, the output capacitor discharges through the electrode 22 for a predetermined duration (typically 0.3-1.5 msec) and the heart is paced. The output capacitor then begins to recharge in preparation for the next pacing pulse.

The power required by the output circuitry 20 and the control circuitry 26 is supplied by a battery, shown generally at 30. As is known in the art, the open circuit voltage, $V_{oc}$, of the battery is reduced by the operating current flowing through the internal battery impedance, $R_{batt}$. Consequently the total voltage available to the pacer circuits at any given time is the battery output voltage, $V_{batt}$. When the battery is fresh, $R_{batt}$ is at a minimum and $V_{batt}$ is at a maximum. As the battery ages $R_{batt}$ increases, thereby reducing the total voltage available $V_{batt}$.

The control circuitry 26, which typically comprises digital circuitry and today may include a microprocessor, requires a constant minimum voltage in order to function properly. However, to increase the useful life of the pacemaker, it is also desirable to keep the voltage powering the control circuitry 26 as low as possible without falling below the minimum operating voltage, thus minimizing the current drain.

The voltage requirements of the output circuitry 20, however, are different. Just after the output capacitor has discharged the output circuitry 20 draws a large amount of current to recharge the output capacitor. On the other hand, when the output capacitor has almost completely charged, the output circuitry 20 draws almost no current. Thus, there is a peak demand for current just after the heart has been paced. This peak demand places a heavy, temporary drain on the battery 30. For this reason, many prior art pacemakers include a capacitor, $C_{batt}$, across the battery to help prevent the temporary load from drawing the battery voltage, $V_{batt}$, below the minimum voltage necessary to operate the control circuitry 26.

Figure 2A:
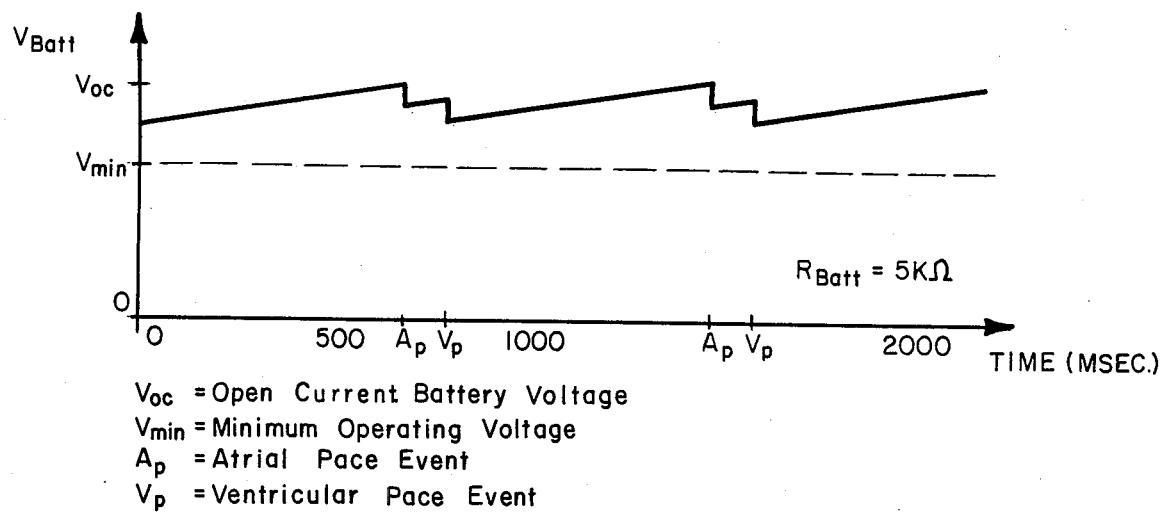
FIG. 2a is a graph illustrating the operational voltage of the prior art pacemaker of FIG. 1 near the middle of its life.
Figure 2B:
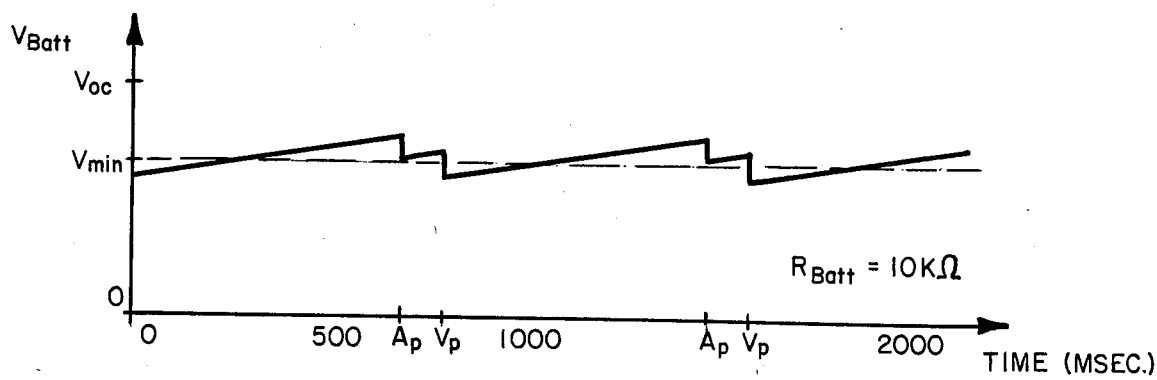
FIG. 2b is a graph illustrating the operational voltage of the prior art pacemaker of FIG. 1 at the end of its useful life.

The disadvantages of prior art pacemakers such as the one illustrated in FIG. 1 can be best understood with reference to FIGS. 2a and 2b. FIG. 2a is a diagram of the battery voltage of the pacemaker of FIG. 1 near the middle of its life when the impedance, $R_{batt}$, of the battery is approximately 5K ohms. In FIG. 2b, the pacemaker is at the end of its useful life and $R_{batt}$ is approximately 10K ohms. $V_{oc}$ indicates the maximum voltage available with a fresh battery. $V_{min}$ indicates the minimum operating voltage for the control circuit. If the output voltage, $V_{batt}$, of the battery drops below this minimum operating voltage at any time, the control circuitry 26 may begin to operate unreliably.

It should be noted that FIGS. 2a and 2b illustrate typical battery voltage wave forms for a dual chambered pacemaker, i.e. a pacemaker which paces both the atria and ventricles. However, the discussion herein applies with equal force to all types of pacemakers, both single and dual chamber and subsequent discussions will not differentiate between the two.

The graph in FIG. 2a illustrates that as the output capacitor charges, the available battery voltage, $V_{batt}$, increases. This is because the output circuit 20 draws less current as the output capacitor becomes fully charged. After the output capacitor discharges to pace the atria, for example at a time $A_p$, the total battery voltage, $V_{batt}$, quickly drops as the output capacitor begins to recharge. The output capacitor then discharges again to pace the ventricles at a later time $V_p$. Again, the total battery voltage, $V_{batt}$, drops suddenly as the output capacitor recharges. Between the pace events, the total battery voltage again rises slowly as the capacitor recharges. This entire process is repeated each time the output capacitor discharges to pace the heart. The sudden drops in battery voltage do not affect the control circuitry 26 when the battery 30 is fresh because the battery's output voltage, $V_{batt}$, never falls below the required minimum operating voltage, $V_{min}$.

Referring now to FIG. 2b, operation of the same dual chambered pacemaker is illustrated as the battery approaches the end of its life. The battery impedance, $R_{batt}$, is 10K ohms. It can be seen that, as the heart is paced, the total available battery voltage, $V_{batt}$, drops below the minimum voltage, $V_{min}$, necessary for proper functioning of the control circuitry 26. Specifically, after the heart has been paced, first at the time $A_P$ and then at the time $V_P$, the increased current demand of the output circuit 20 draws the battery voltage $V_{batt}$ below $V_{min}$. When $V_{batt}$ is below $V_{min}$, the control circuitry 26 may not function reliably. This can cause unpredictable and perhaps dangerous results. Therefore, the pacemaker must be replaced even though the battery's average output voltage is greater than $V_{min}$ and is still sufficient to provide the requisite energy to stimulate the heart.

FIGS. 2a and 2b illustrate that the pacemaker is operating inefficiently because the voltage powering control circuitry 26 is typically greater than the minimum voltage which is required. Since the increased voltage does not enhance the performance of the control circuit, the excess power drawn is simply wasted.

Figure 3:
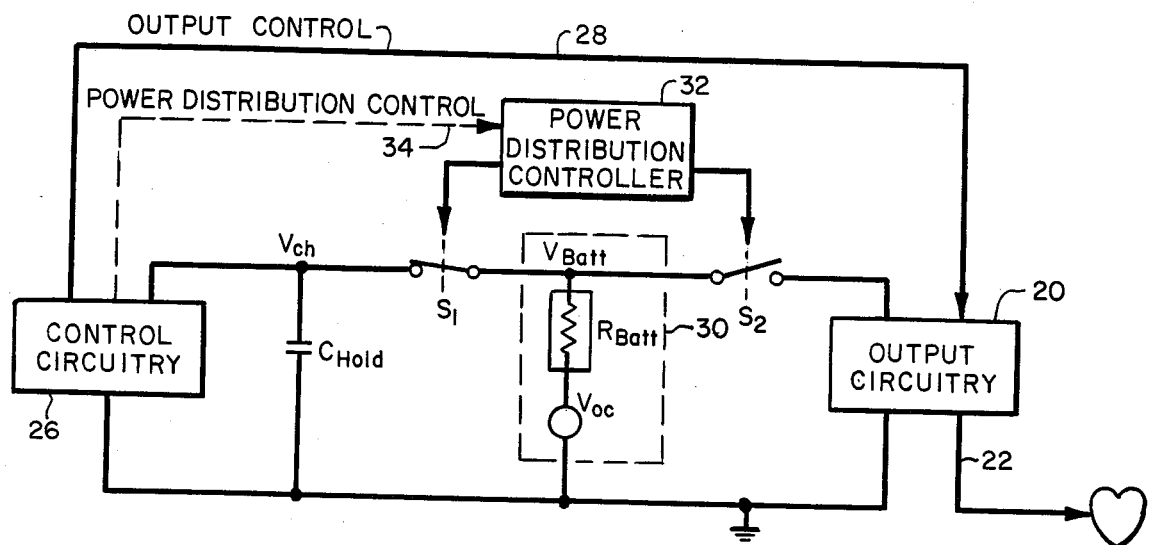
FIG. 3 is a diagrammatic illustration of a pacemaker circuit embodying the invention.

The difficulties with the prior art pacemakers may be overcome using the device illustrated diagramatically in FIG. 3. It should be understood that the power control system disclosed in FIG. 3 and hereafter in the specification is not confined solely to pacemaker applications. It may be used in any type of body function assistance device that has control circuitry which must be kept above a minimum voltage. This system may also be used, for example, in muscle stimulators, nerve stimulators or drug infusion pumps. In addition, the invention would also provide the same advantages in any system which has one power source which supplies two loads, a first load for performing a predefined function, and a control circuit load for controlling the operation of the first load wherein the voltage powering the control circuit must be kept above a minimum voltage. The embodiments disclosed herein are described in the context of a pacemaker for illustrative purposes only.

The pacemaker circuit of FIG. 3 overcomes the disadvantages of the prior art by selectively isolating the control circuitry 26 and the output circuitry 20 from the battery 30 with switches $S_1$ and $S_2$. In operation, a power distribution controller 32 causes the switches $S_1$ and $S_2$ to switch the battery 30 between the control circuit 26 and the output circuit 20. The controller 32 may be controlled by distribution control signals which are generated by the control circuit 26 and applied over control lines 34. The control circuitry 26 may thus synchronize the operation of the power distribution controller 32 with the operation of the pacemaker.

The switches $S_1$ and $S_2$ are operated to distribute power between the control circuit 26 and the output capacitor of the output circuit 20, so that the peak power requirement of the output capacitor does not affect the supply voltage, $V_{ch}$, of the control circuit. In the preferred embodiments, the switch $S_1$ is opened to disconnect the control circuit 26 from the battery 30 whenever the switch $S_2$ is closed to connect the battery across the output capacitor of the output circuit 20. While the output capacitor is charging, a hold-up capacitor $C_{hold}$ maintains the voltage at $V_{ch}$ at or above the minimum required voltage $V_{min}$ for powering the control circuit 26. After a predetermined interval, or as required, the switch $S_2$ is opened to disconnect the battery from the output capacitor of the output circuit 20 and the switch $S_1$ is closed to connect the battery to the control circuit 26 and the capacitor $C_{hold}$.

It will be clear to those skilled in the art, however, that many sequences of opening and closing switches $S_1$ and $S_2$ may be used to ensure that a minimum operating voltage is maintained across the control circuitry 26. For example, the voltage across the control circuitry 26 may be monitored and switches $S_1$ and $S_2$ closed simultaneously except when the voltage across the control circuitry 26 drops below a predetermined minimum voltage. Many other variations are also possible and will occur to those skilled in the art.

The switches $S_1$ and $S_2$ may be operated so that priority is given to maintaining a minimum operating voltage on the control circuit 26. In such a system, $S_1$ is closed until $C_{hold}$ is charged to the voltage $V_{ch}$ required for the powering the control circuit 26. Thereafter, $S_1$ is opened and $S_2$ is closed, so that the output capacitor of the output circuit 20 begins to charge and the capacitor $C_{hold}$ sustains the voltage powering the control circuit 26. When the voltage, $V_{ch}$, on the capacitor $C_{hold}$ drops below a predetermined level, the power distribution controller 32 closes the switch $S_1$ and opens the switch $S_2$ to recharge the capacitor $C_{hold}$, regardless of the requirements of the output circuitry 20. When the capacitor $C_{hold}$ is again charged, the switches $S_1$ and $S_2$ are again operated to continue charging the output capacitor. This charging cycle ensures that the control circuit 26 receives enough voltage to operate reliably.

The operation of the power control system will be further described in conjunction with four embodiments disclosed hereafter. It is to be understood that the four embodiments are provided by way of example only and are not limiting implementations. For example, the disclosed circuits may also be implemented using solid state integrated circuitry without departing from the invention.

Figure 4:
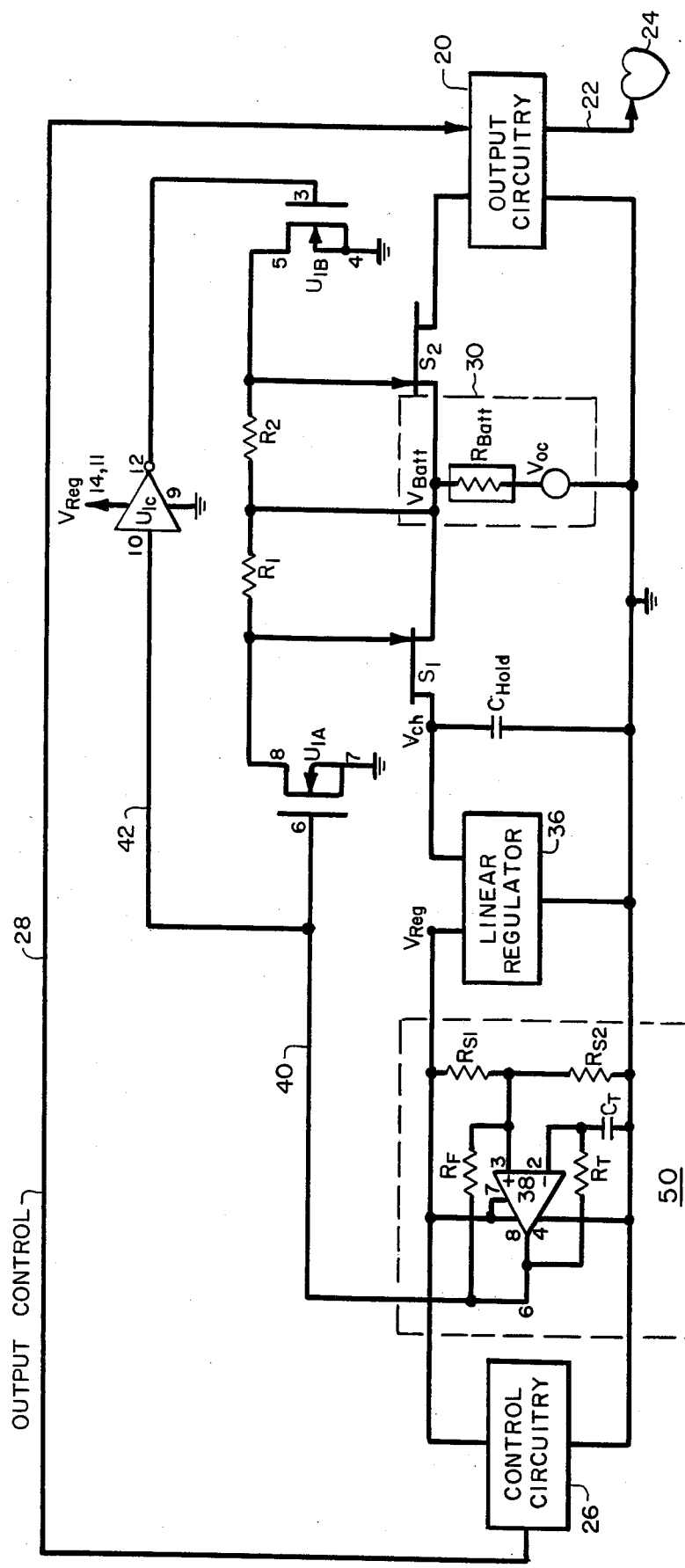
FIG. 4 is a circuit diagram of a first embodiment of the invention.

A first embodiment of a power control system for a heart pacer is shown in FIG. 4. The power distribution controller includes a fixed duty-cycle oscillator 50 which opens and closes switch $S_1$ while simultaneously closing and opening switch $S_2$.

The oscillator 50 is designed to close switch $S_1$ long enough so that, even at the predicted end of life battery voltage, the capacitor $C_{hold}$ can maintain the voltage powering the control circuit 26 above its minimum operating voltage.

The power control system of FIG. 4 only works reliably if its frequency and duty cycle are computed for the predicted end of life conditions of the battery. To make these calculations, it is necessary to know the current drain and voltage requirements of the control circuit, and the end of service battery impedance. If these values are known, one skilled in the art can calculate the time needed to charge the capacitor $C_{hold}$ as the battery 30 nears the end of its useful life, and the amount of time for the capacitor $C_{hold}$ to discharge when it is disconnected from the battery 30 so that the voltage powering the control circuit drops to its minimum operating voltage. The amount of time to charge the capacitor $C_{hold}$ at the end of the battery's life is, of course, the maximum charging time that will be necessary throughout the life of the pacemaker. Consequently, if the end of life charge time is always used to charge the capacitor $C_{hold}$, the capacitor will be properly charged throughout the pacemaker's life. Thus, once the end of life charge time and discharge time have been computed, the frequency and duty cycle of the oscillator may be determined.

The operation of the circuit of FIG. 4 may be best understood with reference to illustrative parameter values for the circuit. Accordingly, it is hereafter assumed for purposes of discussion that the control circuitry 26 requires 2.2 volts and has a current drain of 10 microamperes, the end of service battery impedance is 10K ohms, the capacitance of $C_{hold}$ is 10 $\mu f$ and the open circuit voltge, $V_{oc}$, of the battery is 2.8 volts. Using these circuit parameters, acceptable end of life charge and discharge times are 1 msec and 5 msec respectively. Consequently, the oscillator must operate such that switch $S_1$ is closed for at least 1 msec and is open for no more than 5 msec.

The frequency of the oscillator can now be calculated using the formula:

$$\text{Frequency} = \frac{1}{T_{on} + T_{off}}$$

$T_{on}$ is the time the transistor switch $S_1$ is on, which, in the example above, is 1 msec. $T_{off}$ is the time the transistor switch $S_1$ is off, 5 msec in the above example. Thus, in the disclosed embodiment:

$$\text{Frequency} = \frac{1}{1 + 5} = 167 \text{ Hz}$$

The duty cycle, the percentage of time the transistor switch $S_1$ is on, can be calculated using the formula:

$$\text{Duty Cycle} = \frac{T_{on}}{T_{on} + T_{off}}$$

Thus, in the disclosed embodiment:

$$\text{Duty Cycle} = \frac{1}{1 + 5} = 16.7\%$$

In order to minimize the current drain from the capacitor $C_{hold}$, a linear regulator 36 is placed between the capacitor $C_{hold}$ and the control circuitry 26. The linear regulator 36 maintains a constant voltage, $V_{reg}$, across the control circuitry 26. The linear regulator output voltage, $V_{reg}$, should be equal to the minimum operating voltage $V_{min}$ of the control circuitry 26 in order to maximize the efficiency of the pacer. This voltage, in the embodiment disclosed, is 2.2 volts.

The oscillator 50 of FIG. 4 has the computed frequency and duty cycle. The oscillator includes an operational amplifier 38, resistors $R_F$, $R_{S1}$, $R_{S2}$ and $R_T$, and a capacitor $C_T$. Resistors $R_{S1}$ and $R_{S2}$ form a voltage divider and are connected between the output of the linear regulator 36 and ground. The noninverting input of the operational amplifier 38 is connected at the junction of the resistors $R_{S1}$ and $R_{S2}$. The noninverting input is also connected to the output of the operational amplifier 38 via the resistor $R_F$. The choice of values for the resistors $R_{S1}$, $R_{S2}$ and $R_F$ determine the duty cycle of the oscillator.

The frequency of the oscillator 50 is controlled by the resistor $R_T$ and the capacitor $C_T$. The resistor $R_T$ is connected between the output and the inverting input of the amplifier 38. The capacitor $C_T$ is connected between the inverting input of the amplifier and ground.

The output of the operational amplifier 38 controls the operation of J-FET switches $S_1$ and $S_2$. In operation, the output of the amplifier 38 is conducted via line 40 to the gate of a transistor $U_{1A}$ and, via line 42, through an inverter $U_{1C}$ to the gate of a transistor $U_{1B}$. The drains of transistors $U_{1A}$ and $U_{1B}$ are connected, respectively, to the gates of transistor switches $S_1$ and $S_2$. The drains of $U_{1A}$ and $U_{1B}$ are also connected to the output of the battery 30 via resistors $R_1$ and $R_2$, respectively.

When the voltage on the noninverting input of the operational amplifier 38 is greater than the voltage at its inverting input, a positive voltage appears at its output. This positive voltage, transmitted via lead 40, turns transistor $U_{1A}$ on and thereby allows current to flow from the battery 30, through the resistor $R_1$ and transistor $U_{1A}$, to ground. Consequently, current flows to the gate of the transistor switch $S_1$ and turns the transistor off. This disconnects the battery 30 from the capacitor $C_{hold}$ and the control circuitry 26. The control circuitry 26 continues to operate, however, and draws current through the linear regulator 36, from the capacitor $C_{hold}$.

The positive voltage of the amplifier 38 is also inverted by the inverter $U_{1C}$ and the low voltage at the output of $U_{1C}$ is applied to the gate of $U_{1B}$ to turn $U_{1B}$ off. As a result, no current flows through the resistor $R_2$ to the gate of transistor switch $S_2$. This causes the transistor switch $S_2$ to conduct, thereby connecting the battery 30 to the output circuitry 20.

The positive voltage at the output of operational amplifier 38 also charges the capacitor $C_T$ via the resistor $R_T$ and causes the voltage at the inverting input of the operational amplifier 38 to increase. When the voltage at the inverting input becomes equal to the voltage at the noninverting input, the output voltage of the operational amplifier 38 drops to zero. This causes the transistor $U_{1A}$ to turn off and thus turns the transistor switch $S_1$ on. At the same time, the low voltage of the amplifier 38 causes a positive voltage to appear at the output of the inverter $U_{1C}$ and thus turns the transistor $U_{1B}$ on and the transistor switch $S_2$ off. The output circuitry 20 is thereby disconnected from the battery 30 and the battery is connected to recharge $C_{hold}$.

When the output of the operational amplifier 38 is zero, the capacitor $C_T$ slowly discharges, and thereby lowers the voltage at the inverting input of the amplifier. The capacitor $C_T$ continues to discharge until the voltage at the inverting input of the amplifier 38 is less than the voltage at the non-inverting input. When this occurs, the output of the amplifier 38 again goes high and causes the states of the transistor switches $S_1$ and $S_2$ to reverse.

The alternate switching of the battery 30 between the circuits 26 and 20 ensures that the recharging of the output capacitor will not affect the operation of the circuit 26. The control circuit 26 of FIG. 4 can therefore operate reliably at battery impedances substantially greater than the end of life battery impedances of prior art control circuits. The useful life of the pacemaker of FIG. 4 is therefore increased.

The following component values have been found to provide satisfactory results in the circuit of FIG. 4. It should be understood that these values are listed for illustrative purposes and are not intended to limit the invention.

$R_{S1}=1.0M \, \Omega$
$R_{S2}=5.6M \, \Omega$
$R_f=8.5M \, \Omega$
$R_t=6.49M \, \Omega$
$R_1=5M \, \Omega$
$R_2=5M \, \Omega$
$C_t=0.0015 \, \mu f$
$C_{hold}=10 \, \mu f$
OpAmp 36=ICL7611
$U_1$=MC14007
$S_1=S_2$=J113

Figure 5:
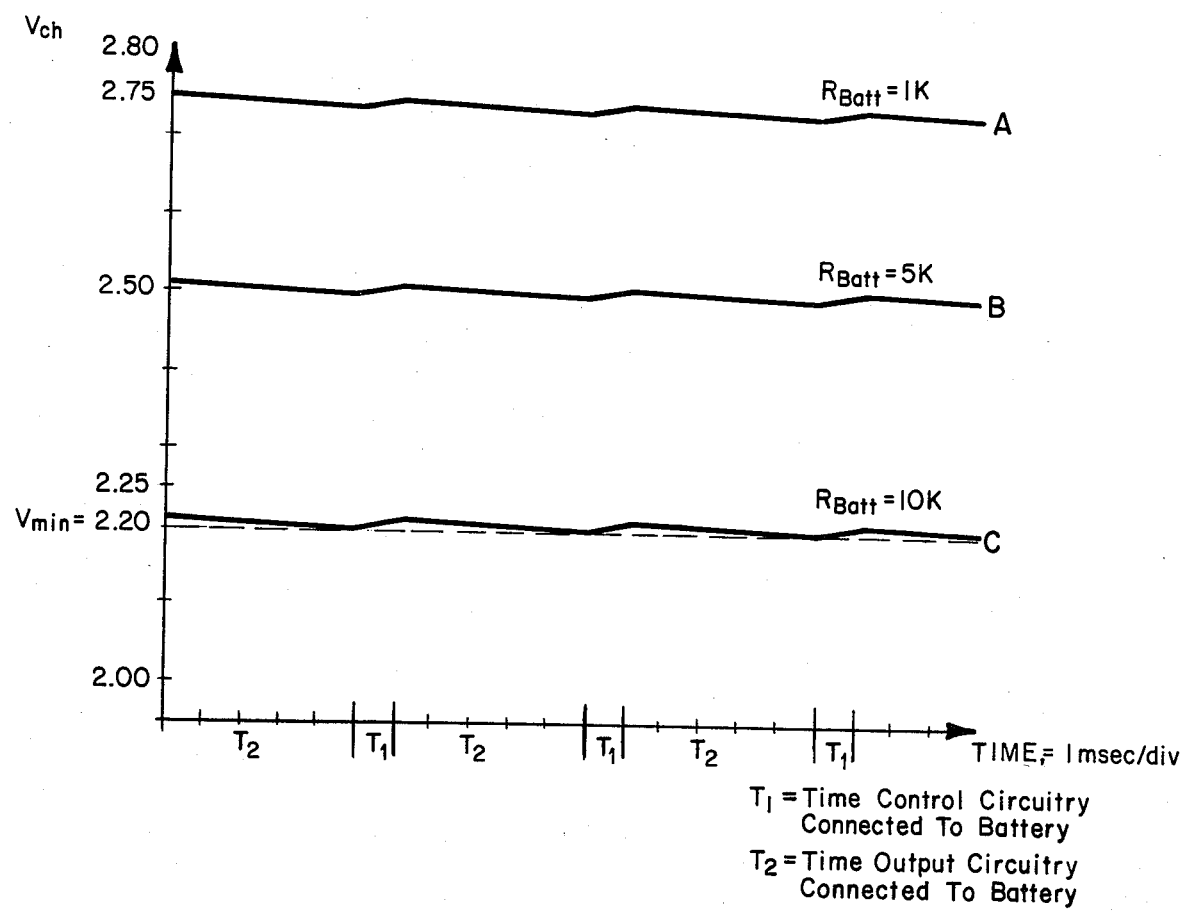
FIG. 5 is a graph illustrating the battery voltage of the pacemaker of FIG. 4 with respect to time.

The enhanced performance achieved by the power control embodiment of FIG. 4 is shown graphically in FIG. 5. The graph plots the voltage $V_{ch}$ across the capacitor $C_{hold}$ vs. time for three different battery impedances.

When the battery 30 is fresh and its impedance is 1K ohm, the voltage $V_{ch}$ across the capacitor $C_{hold}$ is as shown in plot A at the top of the graph. During times $T_2$, the transistor switch $S_1$ is open and the capacitor $C_{hold}$ and control circuitry 26 are disconnected from the battery 30. The capacitor $C_{hold}$ thus discharges slowly and provides current sufficient to run the control circuitry 26. During times $T_1$, the transistor switch $S_1$ is closed and $C_{hold}$ is recharged. As can be seen, the voltage $V_{ch}$ on the capacitor $C_{hold}$ fluctuates slightly at around 2.75 volts.

As the battery ages and its impedance increases, the total voltage across the capacitor $C_{hold}$ decreases. Thus, when the battery impedance $R_{batt}$ is 5K ohms, the voltage $V_{ch}$ across the capacitor $C_{hold}$ is as shown in plot B in the middle of the graph. Because the battery impedance $R_{batt}$ has increased, the available voltage, $V_{batt}$, is less. Consequently, the capacitor $C_{hold}$ can not charge to as great a voltage in the same amount of time. Thus, the voltage $V_{ch}$ on the capacitor $C_{hold}$ drops to approximately 2.5 volts.

Plot C at the bottom of the graph illustrates that, even when the battery impedance $R_{batt}$ is 10K ohms, the charge on the capacitor $C_{hold}$ never dips below the 2.2 volts required to reliably operate the control circuitry 26. Thus, it is clear that a pacemaker incorporating the circuit of FIG. 4 would continue to operate reliably even with a battery impedance of 10K ohms.

Figure 6:
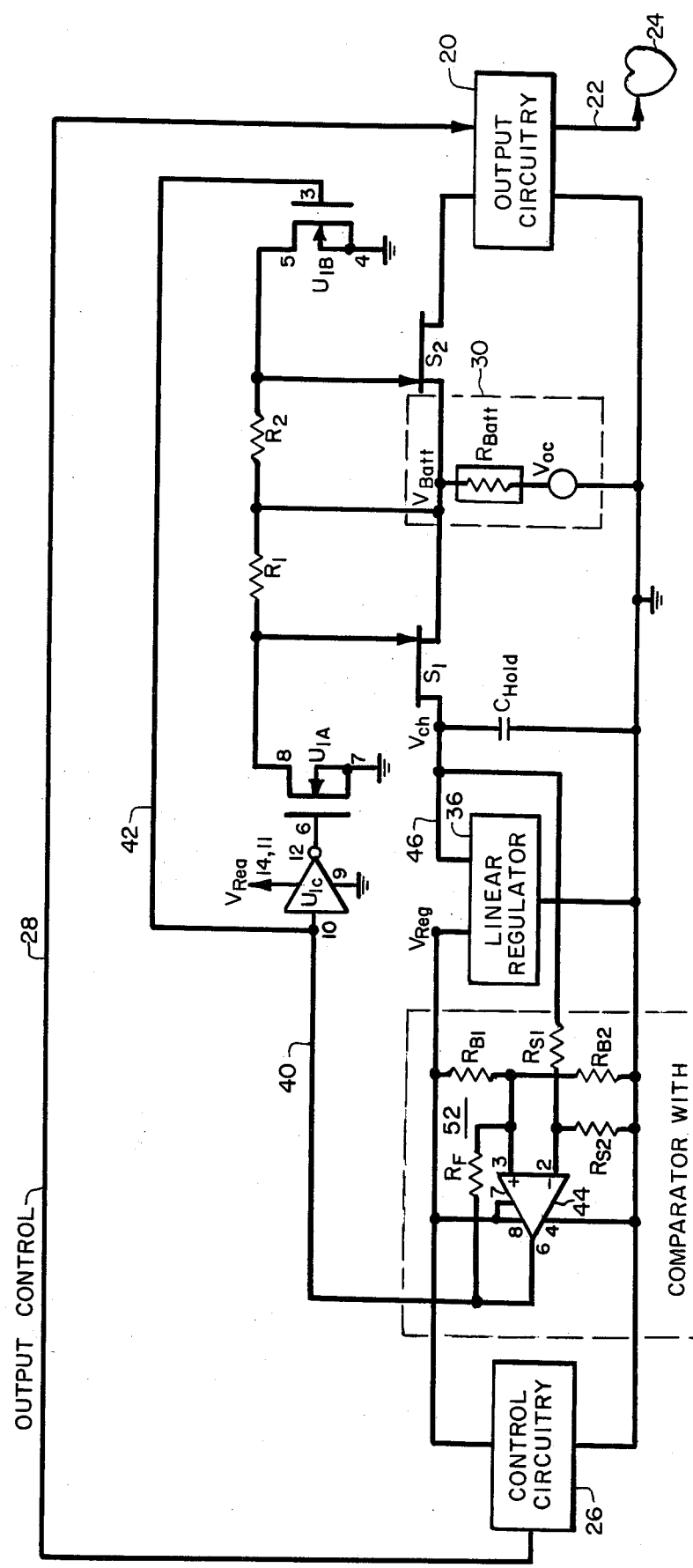
FIG. 6 is a circuit diagram of a second embodiment of the invention.

FIG. 6 illustrates a second embodiment of the power control system of the present invention. The second embodiment is similar to the first, except that the fixed frequency oscillator 50 has been replaced by a comparator 52 with hysteresis.

Although the power control system of FIG. 4 performs substantially better than prior art systems, it has some drawbacks. For example, at high battery impedances, the oscillator 50 fails to give the control circuitry 26 priority over the output circuitry 20. As a result, when the battery impedance increases beyond its predicted end of life impedance, the voltage $V_{ch}$ across the capacitor $C_{hold}$ will dip below the minimum necessary operating voltage, $V_{min}$. The result is a loss of reliability.

The power control system of FIG. 6 overcomes this difficulty by providing the comparator 52 to sense the voltage $V_{ch}$ on the capacitor $C_{hold}$. If the voltage, $V_{ch}$, drops below a predetermined minimum, the comparator 52 causes the switch $S_1$ to close and thereby connects the battery 30 to the capacitor $C_{hold}$. As the capacitor $C_{hold}$ charges, its voltage $V_{ch}$ rises. When the voltage $V_{ch}$ reaches a predetermined maximum, the comparator 52 opens the switch $S_1$ and thereby disconnects the battery 30 from the capacitor $C_{hold}$. Thus, the operation of the comparator 52 insures that a minimum operating voltage is always available for the control circuitry 26. As in the first implementation, the switch $S_2$ is preferably closed whenever the switch $S_1$ is open and vice versa. Thus, the control circuitry 26 is always isolated from the output circuitry 20 and the voltage demands of the output circuit 20 therefore do not affect the operation of the circuit 26.

As the battery 30 ages, the duty cycle of the power distribution circuitry of FIG. 6 increases. Thus, when the battery 30 is fresh, the switch $S_1$ will be closed a relatively small amount of time while the battery 30 charges the capacitor $C_{hold}$ to its predetermined maximum voltage. When the battery 30 is near its end of life, however, the switch $S_1$ will be closed the majority of the time, since the battery 30, with its high internal impedance, will charge the capacitor $C_{hold}$ more slowly. Eventually, the battery 30 will be unable to charge the capacitor $C_{hold}$ to the predetermined maximum value and the switch $S_1$ will remain closed continuously, thereby insuring that the control circuitry 26 has power as long as the battery 30 is able to supply it.

The comparator 52 of FIG. 6 has an operational amplifier 44 and resistors $R_{S1}$, $R_{S2}$, $R_{B1}$, $R_{B2}$, and $R_F$. The resistors $R_{S1}$ and $R_{S2}$ are connected in series between the positive side of the capacitor $C_{hold}$ and ground to act as a voltage divider. The inverting input of the operational amplifier 44 is connected to the junction of the resistors $R_{S1}$ and $R_{S2}$. The noninverting input of the operational amplifier 44 is also connected to a voltage divider which consists of resistors $R_{B1}$ and $R_{B2}$ connected in series between the output of the linear regulator 36 and ground. The output of the operational amplifier 44 is fed back to its noninverting input through the resistor $R_F$.

The output of the operational amplifier 44 is also transmitted, via line 40, to the input of the inverter $U_{1C}$ and, via line 42, to the gate of the transistor $U_{1B}$. The output of the inverter $U_{1C}$ is connected to the gate of the transistor $U_{1A}$. The output of the battery 30 is connected to the gate of the transistor switch $S_1$ through the resistor $R_1$ and to ground through the transistor $U_{1A}$. Likewise, the output of the battery 30 is connected to the gate of the transistor switch $S_2$ through the resistor $R_2$ and to ground through the transistor $U_{1B}$.

The voltage divider $R_{B1}$ and $R_{B2}$, connected at the noninverting input of the operational amplifier 44, receives a constant regulated voltage, $V_{reg}$, from the output of the linear regulator 36. This input to the operational amplifier 44 acts as a reference voltage. This reference voltage is compared with the voltage $V_{ch}$ of the capacitor $C_{hold}$, which is applied to the inverting input of the operational amplifier 44 by the voltage divider of $R_{S1}$ and $R_{S2}$. The resistor $R_F$ creates a hysteresis effect by returning a portion of the output voltage of the amplifier 44 to its noninverting input. The hysteresis effect, in turn, determines the maximum and minimum voltages at which the comparator's output will change from high to low and vice versa.

If the voltage on the inverting input of the operational amplifier 44 is greater than the voltage on its noninverting input, the amplifier's output voltage will be approximately zero. This zero voltage is applied to the input of the inverter $U_{1C}$ to force the output of the inverter $U_{1C}$ to a positive voltage. This positive voltage is transmitted to the gate of the transistor $U_{1A}$ to turn the transistor $U_{1A}$ on. The resulting current flow through the resistor $R_1$ to the gate of the transistor switch $S_1$ turns $S_1$ off, and thus disconnects the battery 30 from the control circuitry 26.

The zero voltage output of the operational amplifier 44 is also applied to the gate of the transistor $U_{1B}$ to turn the transistor off. As a result, the transistor switch $S_2$ turns on, and connects the battery 30 to the output circuitry 20.

When the transistor switch $S_1$ turns off, no current flows from the battery 30 to either the capacitor $C_{hold}$ or the control circuitry 26. Thus, the capacitor $C_{hold}$ discharges through line 46 and through the linear regulator 36 to the control circuitry 26. As in the embodiment of FIG. 4, the linear regulator 36 ensures that a minimum voltage, $V_{reg}$, is provided across the control circuitry 26.

As the capacitor $C_{hold}$ discharges, the voltage at the inverting input of the operational amplifier 44 decreases. When the voltage at the inverting input drops below the voltage at the noninverting input, a positive voltage appears at the amplifier's output. This causes the transistor $U_{1A}$ to turn off and the transistor $U_{1B}$ to turn on, thereby turning the transistor switch $S_1$ on and the transistor switch $S_2$ off, respectively. The battery 30 is thus connected to the capacitor $C_{hold}$, which begins to recharge, and disconnected from the output circuitry 20.

As the charge on $C_{hold}$ increases, the voltage at the inverting input of the operational amplifier 44 again rises. The reference voltage at the noninverting input of the operational amplifier 44, however, is now greater than it was while the the operational amplifier's output was zero. This is because some of the positive output voltage is fed back through the resistor $R_F$ to the noninverting input of the operational amplifier 44. As a result, a hysteresis effect is introduced and the voltage on $C_{hold}$ must rise to a predetermined maximum voltage before the output of the operational amplifier 44 will again drop to zero. In the embodiment of FIG. 6, the following component values and types of semiconductor components have been found to provide a minimum voltage of 2.3 volts and a maximum voltage of 2.4 volts. These values and components are recited for illustrative purposes and are not intended to limit the invention.

Figure 7A:
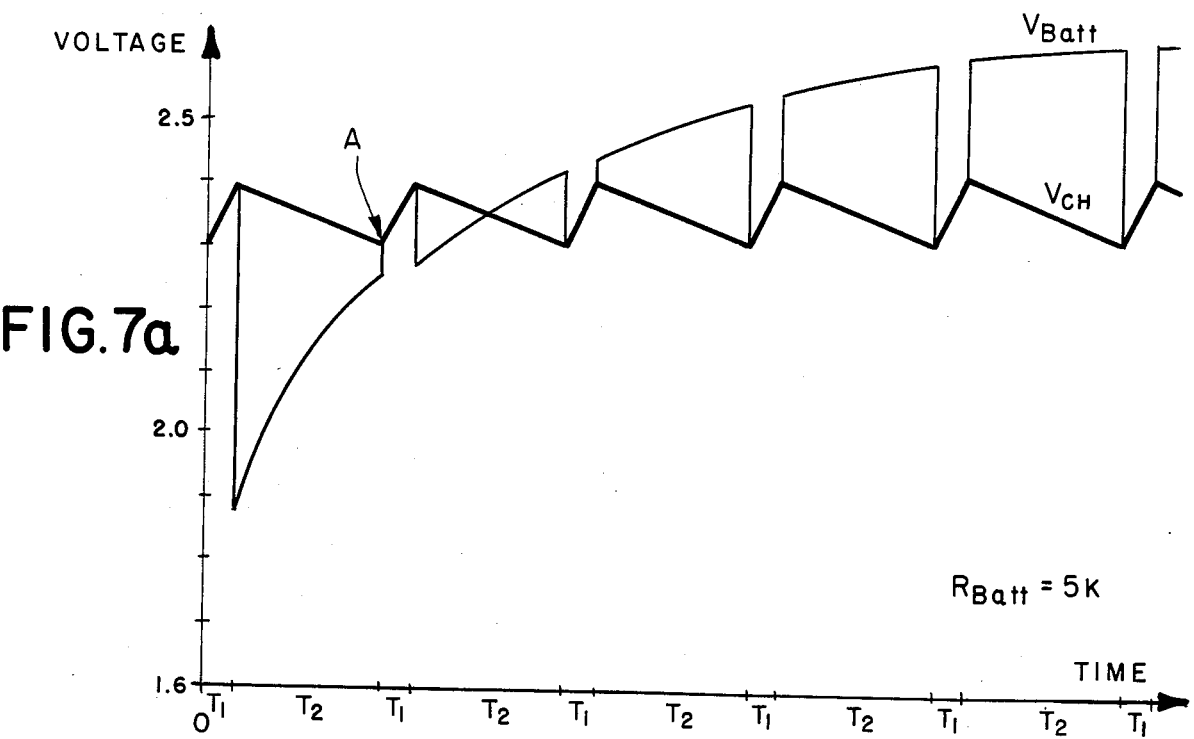
FIG. 7a is a graph illustrating the operational voltage of the pacemaker of FIG. 6 near the middle of its life.
Figure 7B:
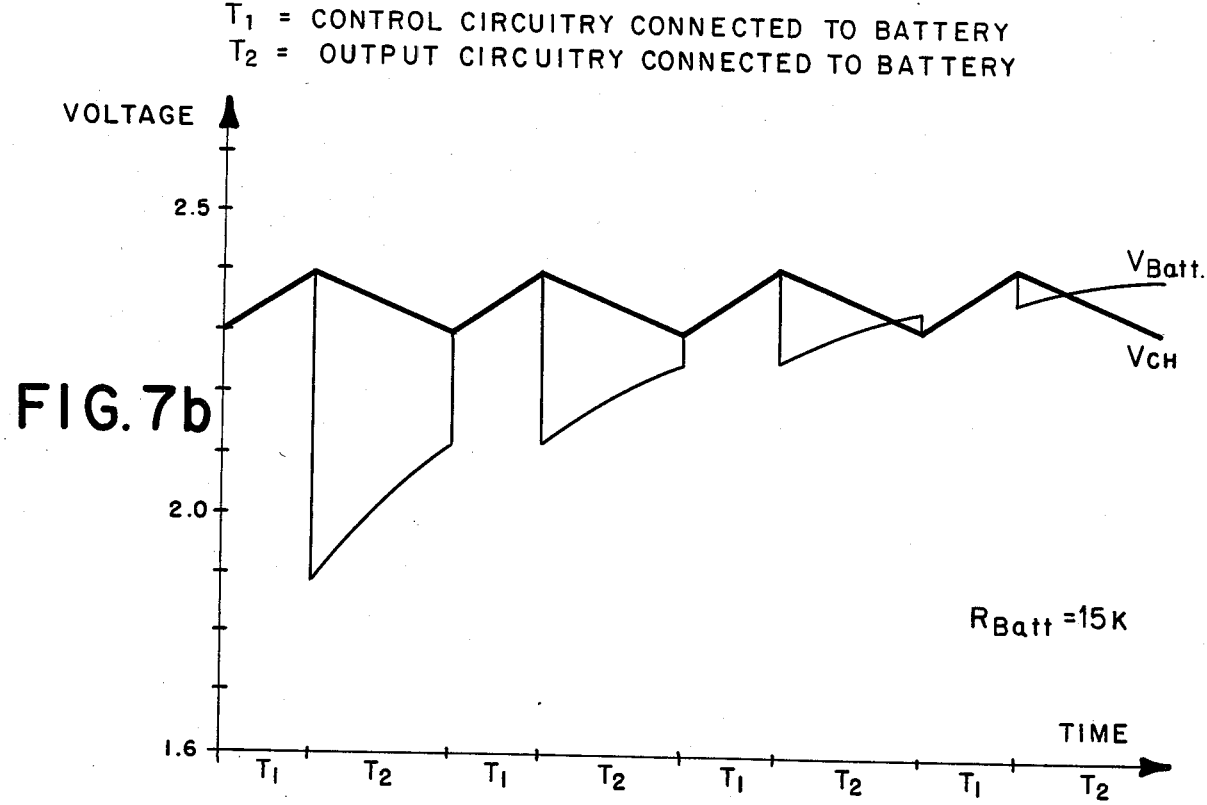
FIG. 7b is a diagram illustrating the operational voltage of the pacemaker of FIG. 6 near the end of its life.

$R_{S1}$ = 2M ohms
$R_{S2}$ = 2M ohms
$R_{B1}$ = 1M ohm
$R_{B2}$ = 1.15M ohm
$R_F$ = 25M ohms
$R_1$ = 5M ohms
$R_2$ = 5M ohms
OP AMP 44 = ICL7611
$U_1$ = MC14007
$S_1 = S_2$ = J113
$V_{oc}$ = 2.8 volts
$V_{reg}$ = 2.2 volts
$C_{hold}$ = 10 μf FIGS. 7a and 7b illustrate graphically the operation of the embodiment of FIG. 6 at two different battery impedances. In these figures, the voltage at $V_{ch}$ is shown as a heavy line, while the voltage at $V_{batt}$ is shown as a thin line. During times $T_1$, the switch $S_1$ is closed and the switch $S_2$ is open. Thus, the battery 30 is charging capacitor $C_{hold}$ and the voltages $V_{batt}$ and $V_{ch}$ rise steadily from 2.3 to 2.4 volts. During times $T_2$, the battery 30 is disconnected from the control circuitry 26 and is connected to charge the output capacitor of the output circuitry 20. During times $T_2$, the voltage $V_{ch}$, on $C_{hold}$, drops from 2.4 volts to 2.3 volts. Meanwhile, the voltage at $V_{batt}$ rises as the output capacitor charges and draws less current.

When the impedance of the battery, $R_{batt}$, is equal to 5K ohms, the voltages at points $V_{batt}$ and $V_{ch}$ are as shown in FIG. 7a. It is clear from this graph that the large battery drain caused by the initial charging of the output capacitor does not affect the voltage $V_{ch}$ powering the control circuit 26. Thus, for example, at point A, although the battery voltage, $V_{batt}$, is low during time $T_2$, it quickly jumps to 2.3 volts at the beginning of time $T_1$. Thus, the effect of charging the output capacitor is not transmitted to the control circuitry 26.

In FIG. 7b, the voltages $V_{batt}$ and $V_{ch}$ are illustrated for a battery impedance, $R_{batt}$, of 15K ohms. As can be seen, the voltage $V_{ch}$ still increases during times $T_1$ from 2.3 to 2.4 volts and decreases during times $T_2$. However, because of the increased battery impedance, it takes longer for the battery 30 to charge the capacitor $C_{hold}$ and thus times $T_1$ are longer. However, the total voltage at $V_{ch}$ is still maintained between 2.3 and 2.4 volts. Since the control circuitry 26 has priority, the battery 30 remains connected to the control circuitry 26 for as long as it takes to charge $C_{hold}$ to its maximum voltage, 2.4 volts.

When FIGS. 7a and 7b are compared, it is apparent that the total voltage, $V_{ch}$, on the capacitor $C_{hold}$ always remains between 2.3 and 2.4 volts regardless of the battery impedance. This can be contrasted with the operation of the first embodiment, shown in FIG. 5. In the embodiment of FIG. 5, as the battery impedance increases, the total voltage available to the control circuitry 26 decreases. The system of FIG. 5 is therefore not as reliable at high battery impedances as the pacemaker system of FIG. 6.

Figure 8:
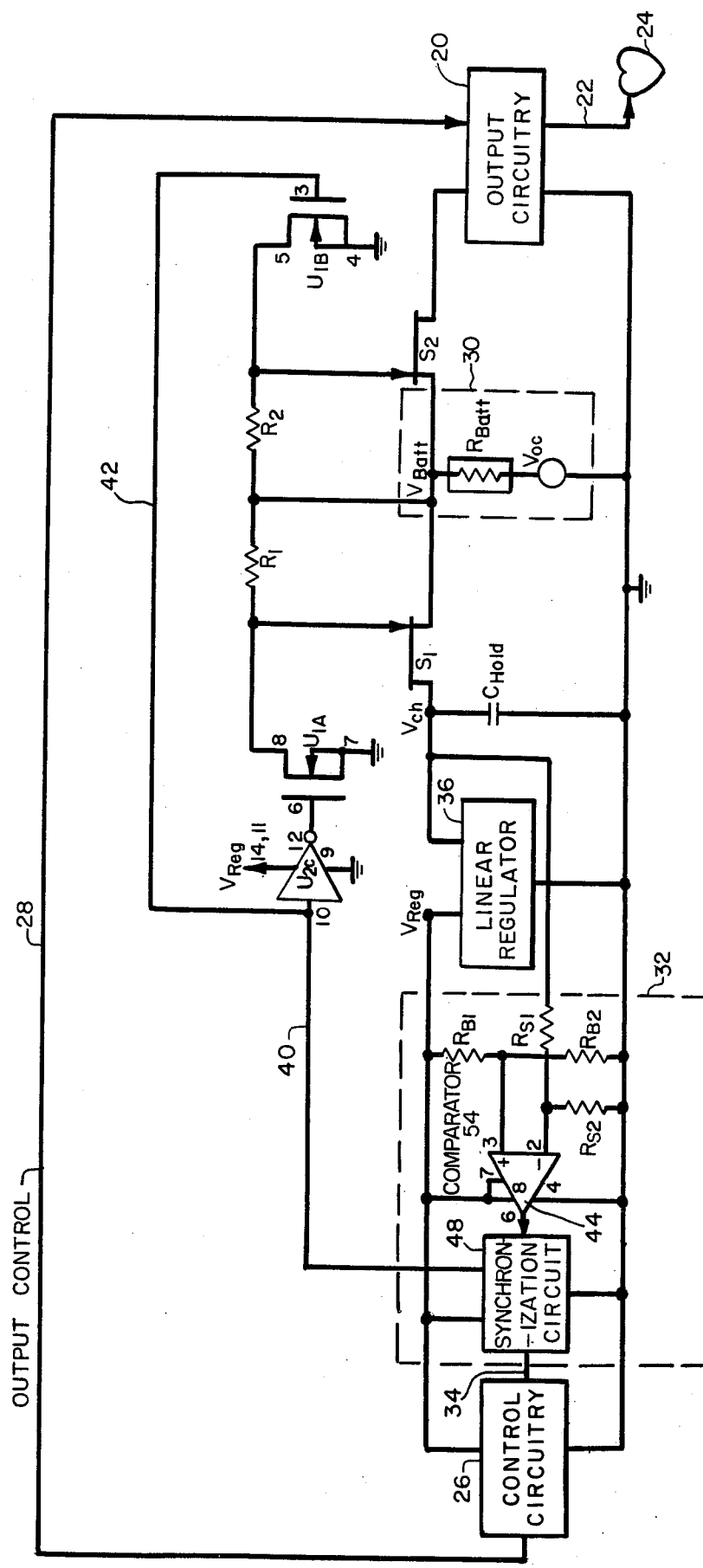
FIG. 8 is a circuit diagram of a third embodiment of the invention.

In a third embodiment of the invention, shown in FIG. 8, a synchronization circuit 48 is used with the comparator 54 of the power distribution controller and controls the operation of switches $S_1$ and $S_2$. The synchronization circuit 48 may comprise discrete logic components. It may be physically included in the control circuitry 26 or provided as an independent component. In the preferred embodiment, interaction between the control circuitry 26, the synchronization circuit 48, and the comparator 54, determines when the switch $S_1$ is closed to connect the battery 30 to capacitor $C_{hold}$.

In the embodiment of FIG. 8, the synchronization circuit 48 receives inputs from the system clock on control lines 34 and the interrupt signal from the comparator 54. In response to these signals, the synchronization circuit 48 generates a control signal on line 40 which controls the operation of transistor switches $S_1$ and $S_2$. Those skilled in the art will realize that such a synchronization circuit may be implemented in various ways. For example, the synchronization circuit 48 could comprise a flip-flop such as a D-type flip-flop with the system clock connected to the clock input of the flip-flop and the interrupt signal to the data input.

An output of the flip-flop could be connected to line 40 to control the operation of switches S1 and S2.

In the embodiment of FIG. 8, the comparator 54 of the power distribution controller 32 is virtually identical to the comparator 52 in the embodiment of FIG. 6. In FIG. 8, however, the comparator 54 does not include the feedback resistor $R_F$ and, therefore, it has no hysteresis. It is identical in all other respects to the comparator 52 of FIG. 6.

The output of the operational amplifier 44, in the embodiment of FIG. 8, is applied as an input to the synchronization circuit 48. Line 40 then carries signals from the synchronization circuit 48 to the input of the inverter $U_{1C}$ and, via line 42, to the gate of the transistor $U_{1B}$. The output of the inverter $U_{1C}$ is applied to the gate of the transistor $U_{1A}$. As in previous embodiments, the battery 30 is connected, through the resistor $R_1$, to the gate of the transistor switch $S_1$ and to ground through the transistor $U_{1A}$. The battery 30 is also connected, through resistor $R_{S1}$, to the gate of the transistor switch $S_2$ and to ground through the transistor $U_{1B}$.

The control circuitry 26, in the four embodiments disclosed herein, may be microprocessor based. In such a system a system clock, not shown, would be included to provide a uniform square wave output as a time base for the microprocessor. In the embodiment of FIG. 8, the output of the system clock is also transmitted via a power distribution control line 34 to the synchronization circuit 48.

At the beginning of each system clock cycle, the synchronization circuit 48 provides a high or a low output on line 40 depending on the input voltage level received from the operational amplifier 44. The synchronization circuit 48 maintains the high or the low output on line 40 until the beginning of the next clock cycle, when it will again set its output in dependence on the input voltage level received from the operational amplifier 44. If the input voltage received from the amplifier 44 is approximately zero volts, the synchronization circuit 48 will provide a low voltage on lead 40 at the beginning of the next clock cycle. This low voltage is transmitted via line 40 to the input of the inverter $U_{1B}$ and, via line 42, to the gate of the transistor $U_{1B}$. The inverter $U_{1C}$ provides a high output to the base of the transistor $U_{1A}$ to turn the transistor on. This opens the transistor switch $S_1$ and thereby disconnects the battery 30 from the capacitor $C_{hold}$. The low voltage at the gate of $U_{1B}$ turns $U_{1B}$ off and thereby closes the transistor switch $S_2$ and connects the output circuitry 20 to the battery 30.

On the other hand, when the output of the operational amplifier 44 is high, the synchronization circuit 48 will provide a high voltage on line 40 at the beginning of the next clock cycle. This will result in the closing of the transistor switch $S_1$ and the opening of the transistor switch $S_2$.

The output of operational amplifier 44 changes state when the voltage appearing at its inverting input rises above or falls below a predetermined voltage which appears at its noninverting input. The predetermined voltage at the noninverting input of the amplifier 44 is a fixed reference voltage. The reference voltage is derived by passing the regulated voltage $V_{reg}$, generated by the linear regulator 36, through a voltage divider comprising resistors $R_{B1}$ and $R_{B2}$. The voltage at the inverting input of the amplifier 44 is proportional to the voltage stored on the capacitor $C_{hold}$. Thus, when the voltage on the capacitor $C_{hold}$ drops below a predetermined switching voltage, $V_{sw}$, the output of the operational amplifier 44 goes high. As described above, the synchronization circuit 48 does not respond to this high voltage output until the beginning of the next clock cycle. Consequently, the capacitor $C_{hold}$ continues to discharge. When the next clock cycle begins, the synchronization circuit 48 responds to the interrupt signal and causes the switch $S_1$ to close and the switch $S_2$ to open. The battery 30 is thus connected to the capacitor $C_{hold}$ and the capacitor $C_{hold}$ recharges.

As the capacitor $C_{hold}$ recharges, the voltage at the inverting input of the operational amplifier 44, which is proportional to the voltage $V_{ch}$ on capacitor $C_{hold}$, rises. When the voltage at the inverting input rises above the reference voltage at the noninverting input, the output of the amplifier 44 drops low. This has no effect on switches $S_1$ and $S_2$, however, until the beginning of the next clock cycle. Until the next cycle begins, switch $S_1$ remains closed and the capacitor $C_{hold}$ continues to charge. When the synchronization circuit 48 responds to the low voltage output at the beginning of the clock cycle, the switches again change state, disconnecting the battery 30 from the capacitor $C_{hold}$ and connecting it to the output circuit 20.

The following component values and types of semiconductor components have been found to provide satisfactory results in the circuit of FIG. 8. These values and devices are provided for illustrative purposes and are not intended to limit the scope of the invention.

Figure 9A:
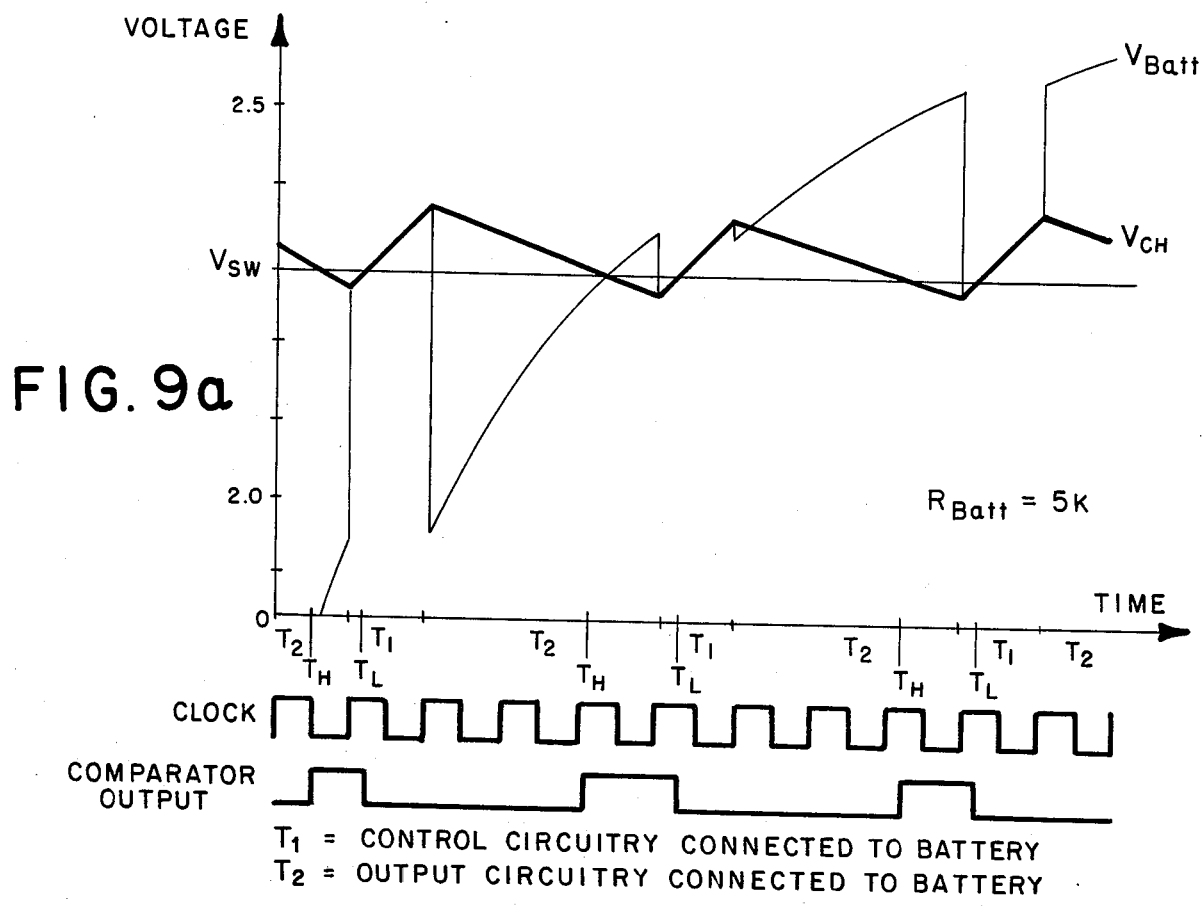
FIG. 9a is a graph illustrating the operation of the pacemaker of FIG. 8 near the middle of its life.
Figure 9B:
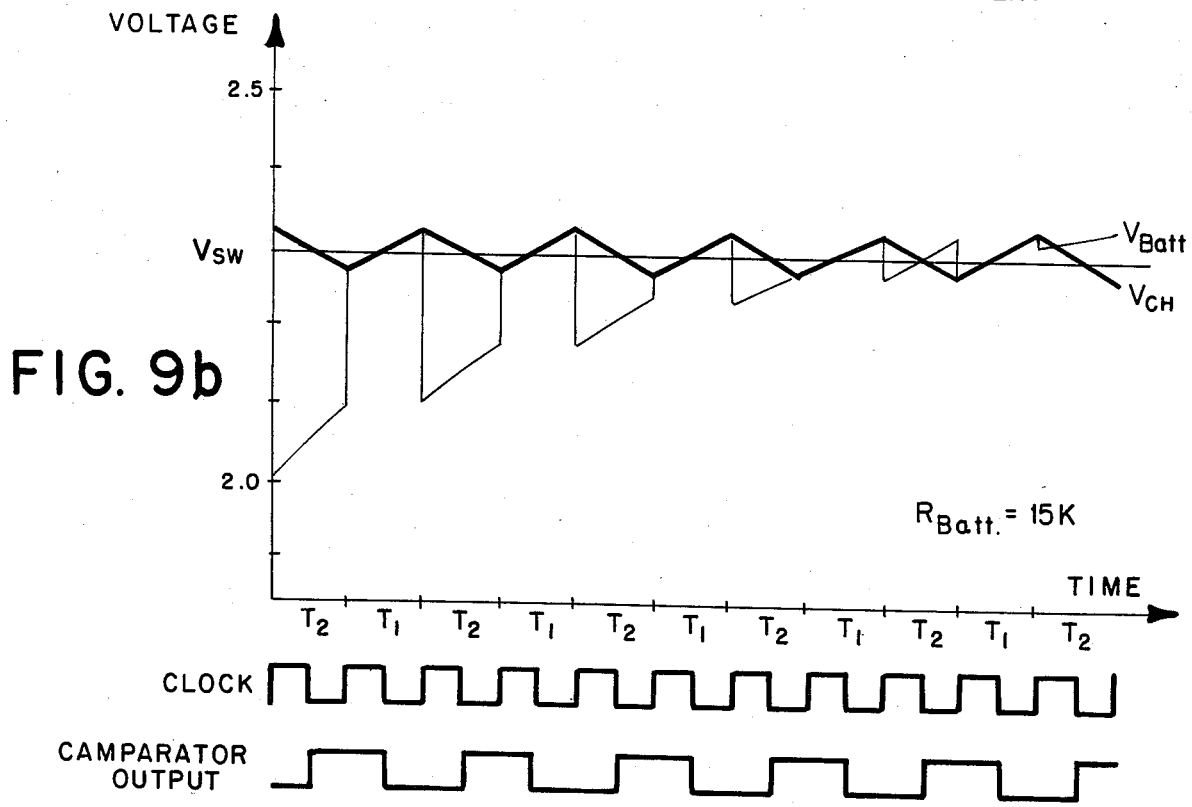
FIG. 9b is a diagram illustrating the operation of the pacemaker of FIG. 8 near the end of its life.

$R_{S1}$ = 2.2MΩ
$R_{S2}$ = 2MΩ
$R_{B1}$ = 2MΩ
$R_{B2}$ = 2MΩ
$R_1$ = 5MΩ
$R_2$ = 5MΩ
$U_1$ = MC14007
OP AMP 44 = ICL7611
$S_1$ = $S_2$ = J113
$C_{hold}$ = 10 μf
$V_{oc}$ = 2.8 V
$V_{reg}$ = 2.2 V The operation of the circuit of FIG. 8 is shown graphically in FIGS. 9a and 9b. In FIG. 9a the battery 30 is near the middle of its service life and the battery impedance, $R_{batt}$, is 5K ohms. At time zero in FIG. 9a, the output of the comparator, shown at the bottom of the FIGURE, is low. Thus, switch $S_1$ is open and the battery 30 is disconnected from the capacitor $C_{hold}$. Meanwhile, the voltage $V_{ch}$ across the capacitor $C_{hold}$ is falling. At time $T_h$, the voltage $V_{ch}$ on the capacitor $C_{hold}$ reaches the predetermined switching voltage $V_{sw}$. When the voltage at $V_{ch}$ is below $V_{sw}$, the proportional voltage appearing at the inverting input of the operational amplifier 44 is below the reference voltage at the noninverting input. This causes the output of the comparator 54 to go high. However, the switch $S_1$ remains open until the beginning of the next clock pulse because the synchronization circuit 48 does not respond to the comparator output until the beginning of the next clock pulse. Thus, until the end of time $T_2$, the voltage at $V_{ch}$ continues to drop.

At the beginning of the next clock pulse, the synchronization circuit 48 responds to the high comparator output and causes the switch $S_1$ to close and the switch $S_2$ to open. As a result, the capacitor $C_{hold}$ recharges and the voltage at $V_{ch}$ rises. During time $T_1$, the voltage $V_{ch}$ on the capacitor $C_{hold}$ rises above the switching voltage $V_{sw}$ and causes the output of the comparator to go low at time $T_L$. However, this does not affect the state of the switches $S_1$ and $S_2$ until the beginning of the next clock cycle. Thus, the capacitor $C_{hold}$ continues to charge until the end of time $T_1$. This process repeats as capacitor $C_{hold}$ discharges and recharges.

The fact that the switches do not operate immediately upon the low output of the comparator 54 results in hysteresis effect similar to the previous embodiment. The amount of hysteresis depends upon the relationship between the system clock interval and the time constant associated with charging $C_{hold}$ (which in turn is dependent upon battery impedance).

FIG. 9b illustrates the operation of the same circuit when the battery impedance, $R_{batt}$, reaches 15K ohms. In FIG. 9b, the battery 30 is connected to the control circuitry 26 on every other clock pulse. This is because the capacitor $C_{hold}$ charges more slowly at higher battery impedance. Thus, the voltage at $V_{ch}$ does not obtain as high a value during one clock pulse as when the battery impedance is 5K ohms. As a result, when the capacitor $C_{hold}$ discharges, $V_{ch}$ falls to the switching voltage $V_{sw}$ more quickly. Thus, at the beginning of every other clock pulse, the comparator output is high and $C_{hold}$ recharges.

It can be seen from FIGS. 9a and 9b that during times $T_2$, the output circuitry 20 is able to draw as much current from the battery 30 as it needs. When the output capacitor first begins to recharge, it draws large amounts of current and causes the battery voltage $V_{batt}$ to drop sharply. When the output capacitor is almost completely recharged, it draws little current and $V_{batt}$ remains high. It is clear, however, that the output capacitor's effects on $V_{batt}$ have no effect on the control circuitry's supply voltage $V_{ch}$. The voltage $V_{ch}$ is consistently maintained at around 2.3 volts.

The circuit design of FIG. 8 gives priority to the control circuitry 26 so that increasing battery impedance will result in proportionately longer times for holding the switch S1 closed and the battery 30 connected to the capacitor $C_{hold}$. Thus, the control circuitry 26 will continue to operate as long as as the output circuit 20 receives any current at all.

Figure 10:
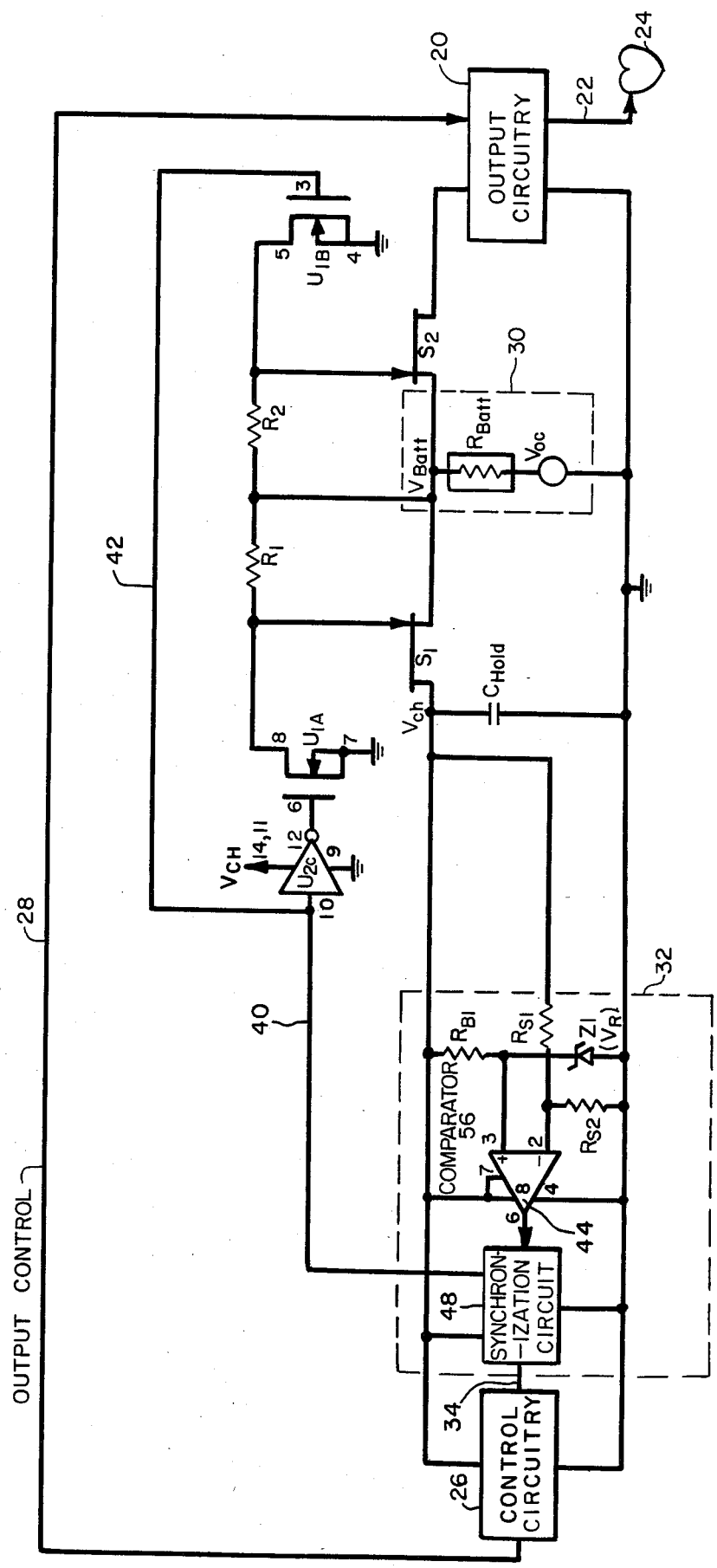
FIG. 10 is a circuit diagram of a fourth embodiment of the invention.

FIG. 10 illustrates a fourth embodiment of the power control system. In this embodiment, the linear regulator used in the previous embodiments has been eliminated. This has the advantage of simplifying the circuit and thereby reducing the pacemaker's complexity. The elimination of the voltage regulator also increases the reliable operational life of the pacer, because the linear regulator itself requires a minimum operating voltage to function properly. If the voltage across the linear regulator drops below this minimum value, it will no longer supply the necessary regulated voltage $V_{reg}$ to the circuits which it powers and the circuits will no longer operate reliably. The minimum voltage required to operate the regulator is, of course, greater than the voltage $V_{reg}$ that it produces and thus greater than the minimum voltage $V_{min}$ required to run the control circuit 26. By eliminating the linear regulator, the voltage at $V_{ch}$ can be allowed to drop to the minimum operating voltage $V_{min}$ of the control circuit 26 and synchronization circuit 48.

There are, of course, some disadvantages to eliminating the linear regulator. The regulator served two functions besides providing a minimum voltage. First, it provided a reference voltage for use by the comparator 54. This problem is easily solved by replacing the resistor $R_{B2}$ with a zener diode $Z_1$ or similar reference. The zener diode $Z_1$ thus assures that a fixed reference voltage is supplied to the comparator 56.

The second function of the linear regulator was to eliminate the fluctuations in voltage that occur as the capacitor $C_{hold}$ discharges and recharges. These voltage fluctuations can be tolerated by the control circuitry 26 and synchronization circuit 48, however, if the maximum voltage fluctuation of $V_{ch}$ is small enough. In the embodiment shown in FIG. 10, the maximum voltage fluctuation, or ripple, occurs when $V_{ch}$ charges most quickly, i.e. at the beginning of the battery's life. The maximum ripple can be calculated using the formula:

$$i\ V_{ripple}=(V_{oc}-V_t)(1-e^{-Tc/(Chold)(Rbatt)})$$

To calculate the maximum ripple for the disclosed embodiment, the following illustrative values are used:
battery voltage, open current $(V_{oc})=2.8$ V
threshold voltage $(V_t)=2.2$ V
system clock period $(T_c)=150$ μsec.
$C_{hold}=10$ μf
battery and switch impedance $(R_{batt})=1K\Omega$ Substituting these values into the formula above results in a voltage fluctuation of 8.9 millivolts for a fresh battery. Such a small ripple will not affect the operation of the control circuitry 26 or the synchronization circuit 48 and, thus, the circuit disclosed in FIG. 10 will operate properly even without the linear regulator. The circuit of FIG. 10 has therefore been modified to be simpler and to extend the longevity of the pacemaker, without sacrificing reliability.

The circuit disclosed in FIG. 10 has been found to operate satisfactorily with the following illustrative component values and types of semiconductor devices, which do not limit the scope of the invention:
$R_{S1}=1M\Omega$
$R_{S2}=1.3M\Omega$
$R_{B1}=1M\Omega$
$R_1=5M\Omega$
$R_2=5M\Omega$
$U_1=MC14007$
OP AMP 44=ICL7611
$S_1=S_2=J113$
$Z_1=1.25$ V zener diode or bandgap reference
$C_{hold}=10$ μf
$V_{oc}=2.8$ V The power distribution controller 32 of FIG. 10 includes the comparator 56 which operates in precisely the same manner as does the comparator of the power distribution controller of FIG. 8. The sole difference is that the system of FIG. 10 will tolerate voltage as low as 2.2 V on the capacitor $C_{hold}$, while the circuit of FIG. 8 will not.

As noted previously, the various embodiments of the power control system disclosed herein function equally well in both single-chamber and dual-chamber pacemakers, with no modification to the power control system. This is true for all four embodiments disclosed. Furthermore, the examples herein included are shown with positive power supplies for simplicity. Pacemakers typically use negative supplies and the invention can also be implemented with a negative supply.

The power control system of the present invention may, of course, be implemented in numerous ways, four of which are disclosed herein. However, the disclosed embodiments are not intended to limit the scope of the invention. Any other adaptations, modifications or embodiments incorporating the invention are expressly deemed to be within the scope of the following claims.

We claim:

1. A power control system, comprising;
   first load means for performing a predefined function;
   second load means;
   power source means for powering the first and second load means; and
   power distribution means for selectively connecting and disconnecting the first load means and the power source means, and for selectively connecting and disconnecting the second load means and the power source means;
   the second load means including an energy storage means for storing power supplied by the power source means when the second load means is connected to the power source means;
   the second load means further including a control means for controlling the operation of the first load means, the control means powered by the power source means when the second load means is connected to the power source means and powered by the energy storage means when the second load means is disconnected from the power source means; and
   the power distribution means including means for comparing the voltage across the energy storage means with a predetermined reference voltage and switch means responsive thereto to connect the second load means to the power source means, so that the voltage powering the control means is maintained above a predetermined operating voltage.

2. The power control system of claim 1 wherein the power distribution means connects the power source means to the second load means and disconnects the power source means from the first load means when the voltage across the energy storage means drops below a predetermined first voltage, and disconnects the power source means from the second load means and connects the power source means to the first load means when the voltage across the energy storage means rises above a predetermined second voltage greater than the first voltage.

3. The power control system of claim 1 wherein the power distribution means includes a means for generating clock pulses and wherein the power distribution means connects the second load means to the power source means and disconnects the first load means from the power source means in response to a clock pulse when the voltage across the energy storage means is below a predetermined switching voltage, and disconnects the second load means from the power source means and connects the first load means to the power source means in response to a clock pulse when the voltage powering the energy storage means is above the predetermined switching voltage.

4. The power control system of claim 1 wherein the energy storage means is a capacitor.

5. The power control system of claim 4 including means for regulating the voltage powering the control means.

6. The power control system of claim 5 wherein the means for regulating is a linear regulator.

7. A power control system for a heart pacemaker, comprising:
   output means for supplying electrical signals to pace the heart;
   control means for controlling the operation of the output means;
   energy storage means for storing electrical energy and powering the control means;
   a power source means for supplying power to the output means, the control means, and the energy storage means; and
   a power distribution means including means for comparing the voltage across the energy storage means with a predetermined reference voltage and switch means responsive thereto for selectively connecting the power source means to the output means and selectively connecting the power source means to the control means and the energy storage means, so that the voltage powering the control means is maintained above a predetermined operating voltage.

8. The power control system of claim 7 wherein the power distribution means connects the power source means to the control means and energy storage means and disconnects the power source means from the output means when the voltage across the energy storage means drops below a predetermined first voltage, and disconnects the power source means from the control means and energy storage means and connects the power source means to the output means when the voltage across the energy storage means rises above a predetermined second voltage greater than the first voltage.

9. The power control system of claim 7 wherein the power distribution means includes a means for generating clock pulses and wherein the power distribution means connects the control means and energy storage means to the power source means and disconnects the output means from the power source means in response to a clock pulse when the voltage across the energy storage means is below a predetermined switching voltage, and disconnects the control means and energy storage means from the power source means and connects the output means to the power source means in response to a clock pulse when the voltage across the energy storage means is above the predetermined switching voltage.

10. The power control system of claim 7 wherein the energy storage means is a capacitor.

11. The power control system of claim 10 including means for regulating the voltage powering the control means.

12. The power control system of claim 11 wherein the means for regulating is a linear regulator.

13. A power control system for a heart pacemaker, comprising:
    battery means;
    output means for supplying electrical signals to pace the heart;
    circuit means including a capacitor for storing energy from the battery means, and control means for controlling the operation of the output means; and
    power distribution means for alternately and selectively switching the battery means between the output means and circuit means in response to the voltage across the capacitor, so that the control means and output means are powered by the battery means when they are respectively connected to the battery means and the control means is powered by the capacitor when the battery means is disconnected from the circuit means.

14. The power control system of claim 13 wherein the power distribution means switches the battery means to the circuit means when the voltage across the capacitor drops below a predetermined first voltage, and the power distribution means switches the battery means to the output means when the voltage across the capacitor rises above a predetermined second voltage greater than the first voltage 15. The power control system of claim 13 including a means for generating clock pulses wherein the power distribution means switches the battery means to the circuit means in response to a clock pulse when the voltage across the capacitor is less than a predetermined switching voltage, and switches the battery means to the output means in response to a clock pulse when the voltage across the capacitor is above the predetermined switching voltage.

16. The power control system of claim 13 including a means for regulating the voltage powering the control means.

17. A method of controlling the power distribution in an electrical system, the system comprising a load means for performing a predefined function, a power source means, an energy storage means, and a control means for controlling the operation of the output means, the method comprising the steps of:
 (a) connecting the power source means to the control means and energy storage means and disconnecting the power source means from the load means;
 (b) powering the control means from the power source means;
 (c) storing energy in the energy storage means from the power source means;
 (d) connecting the power source means to the load means and disconnecting the power source means from the control means and energy storage means in response to the voltage across the energy storage means;
 (e) powering the load means from the power source means; and
 (f) repeating steps (a)-(e) to maintain the voltage across the energy storage means above a predetermined operating voltage.

18. The method of claim 17 wherein steps (a) through (c) are executed when the voltage across the energy storage means drops below a predetermined first voltage; and steps (d) through (e) are executed when the voltage across the energy storage means rises above a predetermined second voltage greater than the first voltage.

19. The method of claim 17 further including the steps of:
 generating a series of clock pulses;
 executing steps (a) through (c) in response to a clock pulse when the voltage across the energy storage means is below a predetermined switching voltage; and
 executing steps (d) through (e) in response to a clock pulse when the voltage across the energy storage means is greater than the predetermined switching voltage.

20. The method of claim 17 further including the step of regulating the voltage powering the control means to reduce voltage fluctuations.

* * * * *